(12) United States Patent
Agnew et al.

(10) Patent No.: US 8,303,649 B2
(45) Date of Patent: Nov. 6, 2012

(54) ARTIFICIAL VENOUS VALVE WITH DISCRETE SHAPING MEMBERS

(75) Inventors: Charles W. Agnew, West Lafayette, IN (US); James B. Hunt, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 627 days.

(21) Appl. No.: 12/021,624

(22) Filed: Jan. 29, 2008

(65) Prior Publication Data

US 2008/0183280 A1 Jul. 31, 2008

Related U.S. Application Data

(60) Provisional application No. 60/897,949, filed on Jan. 29, 2007.

(51) Int. Cl.
*A61F 2/24* (2006.01)
(52) U.S. Cl. ........................ 623/1.24; 623/1.13
(58) Field of Classification Search .............. 623/1.24, 623/1.26, 2.1–2.19, 1.13
See application file for complete search history.

(56) References Cited

U.S. PATENT DOCUMENTS

| 4,643,732 | A | 2/1987 | Pietsch et al. | 623/2.2 |
|---|---|---|---|---|
| 5,314,473 | A | 5/1994 | Godin | |
| 5,500,014 | A * | 3/1996 | Quijano et al. | 623/1.24 |
| 5,851,232 | A * | 12/1998 | Lois | 623/1.13 |
| 6,200,336 | B1 | 3/2001 | Pavcnik et al. | 623/1.15 |
| 6,235,050 | B1 * | 5/2001 | Quiachon et al. | 623/1.11 |
| 6,287,330 | B1 * | 9/2001 | Johansson et al. | 623/1.13 |
| 6,299,636 | B1 | 10/2001 | Schmitt et al. | 623/1.2 |
| 6,299,637 | B1 | 10/2001 | Shaolian et al. | 623/1.24 |
| 6,478,819 | B2 | 11/2002 | Moe | 623/2.18 |
| 2002/0177894 | A1 * | 11/2002 | Acosta et al. | 623/1.24 |
| 2003/0040792 | A1 | 2/2003 | Gabbay | 623/2.11 |
| 2003/0055492 | A1 | 3/2003 | Shaolian et al. | 623/1.24 |
| 2004/0093070 | A1 | 5/2004 | Hojeibane et al. | 623/1.15 |
| 2004/0186558 | A1 | 9/2004 | Pavcnik et al. | 623/1.24 |
| 2004/0225352 | A1 | 11/2004 | Osborne et al. | 623/1.24 |
| 2004/0260389 | A1 * | 12/2004 | Case et al. | 623/1.24 |
| 2005/0033398 | A1 * | 2/2005 | Seguin | 623/1.11 |
| 2005/0143801 | A1 * | 6/2005 | Aboul-Hosn | 623/1.11 |
| 2005/0143807 | A1 | 6/2005 | Pavcnik et al. | 623/1.24 |
| 2005/0187614 | A1 | 8/2005 | Agnew | 623/1.24 |
| 2006/0265053 | A1 | 11/2006 | Hunt | 623/1.24 |
| 2007/0244545 | A1 * | 10/2007 | Birdsall et al. | 623/1.26 |

FOREIGN PATENT DOCUMENTS

FR 2828091 A1 2/2003
WO WO 01/66043 A1 9/2001

OTHER PUBLICATIONS

International Search Report for corresponding PCT Application No. PCT/US2008/052286, dated Jun. 17, 2008.
Written Opinion for corresponding PCT Application No. PCT/US2008/052286, dated Jun. 17, 2008.
PCT Notification Concerning Transmittal of International Preliminary Report on Patentability for PCT/US2008/052286, Aug. 13, 2009.

* cited by examiner

*Primary Examiner* — Christopher D Koharski
*Assistant Examiner* — Rebecca Preston
(74) *Attorney, Agent, or Firm* — Buchanan Nipper LLP (57) ABSTRACT

The invention relates to a prosthetic valve for regulating flow through a body lumen. The medical device comprises discrete shaping members, a flexible covering, and a valve member. The discrete shaping members are operatively attached to the flexible covering, such that the medical device may exhibit low radial force and dynamic movement.

21 Claims, 8 Drawing Sheets

ARTIFICIAL VENOUS VALVE WITH DISCRETE SHAPING MEMBERS

RELATED APPLICATIONS

This application claims the benefit of provisional U.S. patent application Ser. No. 60/897,949, filed Jan. 29, 2007, which is incorporated herein by reference in its entirety.

BACKGROUND

The venous system includes a multitude of one-way bicuspid valves that permit substantially unidirectional blood to flow toward the heart. These valves are particularly important in the lower extremities to prevent the pooling of blood. When the leaflets of the bicuspid valves fail to close properly, the valve is considered "incompetent" as it permits leakage of retrograde flow resulting in the abatement of flow towards the heart.

This potentially serious condition is known as "chronic venous insufficiency." Symptoms can progress from unsightly "spider" or varicose veins to skin discoloration and painful skin ulcerations. The etiology of venous insufficiency is multifactorial, including a past history of thrombotic events, chronic venous stasis, and venous hypertension. Current treatments for venous insufficiency include elevation of the feet and compression stockings. While these can relieve symptoms, the underlying disease remains untreated. Surgical techniques are also employed in which native valves can be bypassed or replaced with autologous sections of veins having functioning valves.

Recently, various implantable medical devices and minimally invasive methods for implantation of these devices have been developed to deliver these medical devices within the lumen of a body vessel. These devices are advantageously inserted intravascularly, for example, from an implantation catheter. For example, implantable medical devices can function as a replacement venous valve, or restore native venous valve function by bringing incompetent valve leaflets into closer proximity. Such devices can comprise an expandable frame configured for implantation in the lumen of a body vessel, such as a vein. Venous valve devices can further comprise features that provide a valve function, such as opposable leaflets.

Dynamic fluctuations in the shape of the lumen of a vein pose challenges to the design of implantable prosthetic devices that conform to the interior shape of the lumen of a vein. Unlike arterial vessels, the flow velocity and diameter of veins does not remain essentially constant at a given systemic vascular resistance. Instead, the shape of vein lumens can fluctuate dynamically in response to the respiration, body position, central venous pressure, arterial inflow and calf muscle pump action of a mammalian subject. The veins also provide the principal volume capacitance organ. For example, an increase of almost 100% in the diameter of the common femoral vein has been observed in human patients simply by rotation of the patient by about 40 degrees, corresponding to a four-fold increase in blood flow volume. Moneta et al., "Duplex ultrasound assessment of venous diameters, peak velocities and flow patterns," J. Vasc. Surg. 1988; 8; 286-291. Therefore, the shape of a lumen of a vein, which is substantially elliptical in cross-section, can undergo dramatic dynamic change as a result of varying blood flow velocities and volumes therethrough, presenting challenges for designing implantable intraluminal prosthetic devices that more closely conform to the changing shape of the vein lumen.

Current implantable devices for treating venous valve insufficiency may exhibit high radial force and be unresponsive to dynamic changes in the shape of a body vessel lumen, such as in a vein. For example, US2003/0055492A1 by Shaolian describes a self-expandable prosthetic venous valve mounted in a support structure exemplified by a plurality of longitudinally connected sinusoidal annular members. US2002/0099439A1 by Schwartz describes devices for radially compressing a vein proximate to an incompetent venous valve to improve or restore valve function. U.S. Pat. No. 6,494,909 to Greenhalgh describes a valve formed by a tube of braided filaments and a portion formed by a plurality of flexible leaflets, which may include fasteners positioned circumferentially around the tube to anchor the valve within the lumen of the vascular vessel. U.S. Pat. No. 6,482,228 to Norred describes an aortic heart valve which is adapted to be placed percutaneously and held in place with a stent system. U.S. Pat. No. 5,855,601 to Bessler describes an artificial heart valve having a stent member with a cylindrical shape and a flexible valve disposed in the stent member. Implantable prosthetic stents or valves for veins often have the same compressibility or expandability in any radial direction. Similarly, implantable device configurations with substantially invariant cross-sections upon implantation can be unresponsive to dynamic changes of the vessel cross-section, and can locally distort the shape of the body vessel.

SUMMARY

The present invention relates to an implantable medical device for regulating fluid flow through a body vessel. More specifically, certain aspects relate to a prosthetic valve comprising a prosthetic valve having a cross-section that can substantially conform to body vessel shapes that have elliptical or circular cross-sections, and can change shape in response to changes in the cross-section of a body vessel. Preferably, the shaping members can be configured to permit movement of the shaping members relative to one another, permitting the prosthetic valve to conform to dynamic changes in a vein shape or movement of the vein wall. The shaping members can have any suitable configuration, including bowed arcuate configurations or bent "V-shaped" configurations.

In one aspect, the prosthetic valve comprises a flexible covering, discrete shaping members, and a valve member. The flexible covering may be a tubular structure defining a lumen with a proximal end and a distal end. The discrete shaping members may be attached to the flexible covering in a manner permitting movement of the shaping members relative to one another. The shaping members may be disposed and configured in a manner permitting compression or expansion of portions of the prosthetic valve in response to movement of a vein. For example, the shaping members may extend partially around the circumference of the tubular member, rather than forming a complete ring around the circumference of the tubular flexible covering structure. In another example, the shaping members may extend longitudinally along the tubular structure, connected to the tubular flexible covering but separate from one another. The valve member may be at least partially positioned within the lumen defined by the flexible covering lumen and be adapted to modify fluid flow through the flexible covering lumen. During radial compression or expansion of the prosthetic valve, the shaping members may move with respect to one another along the surface of the plane defined by a tubular flexible covering structure, which may have a tubular or spherical configuration.

In operation, one can deliver a prosthetic valve in accordance with the present invention transluminally into the selected portion of the body lumen and radially expanding the prosthetic valve until it contacts the body lumen. Transluminal delivery can be accomplished by a catheter designed for such delivery. Radial expansion can be accomplished by balloon expansion of the support frame, by self-expansion of the support frame, or a combination of the foregoing.

DETAILED DESCRIPTION

The following detailed description and appended drawings describe and illustrate various exemplary embodiments of the invention. Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The term "implantable" refers to an ability of a medical device to be positioned at a location within a body, such as within a body lumen.

As used herein, the term "body vessel" means any tube-shaped body passage lumen that conducts fluid, including but not limited to blood vessels such as those of the human vasculature system, esophageal, intestinal, billiary, urethral and ureteral passages.

The terms "about" or "substantially" used with reference to a quantity includes variations in the recited quantity that are equivalent to the quantity recited, such as an amount that is insubstantially different from a recited quantity for an intended purpose or function.

The term "alloy" refers to a substance composed of two or more metals or of a metal and a nonmetal intimately united, for example by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Medical Devices

In one aspect, prosthetic valves may comprise discrete shaping members, a flexible covering, and at least one valve member. The prosthetic valve may be any medical device that is introduced temporarily or permanently into the body for the prophylaxis or therapy of a medical condition. For example, such prosthetic valves may include, but are not limited to, heart valve prostheses, venous valve prostheses, and artificial organs such as artificial hearts. Typical subjects (also referred to herein as "patients") are vertebrate subjects (i.e., members of the subphylum cordata), including, mammals such as cattle, sheep, pigs, goats, horses, dogs, cats and humans.

Figure 1A:
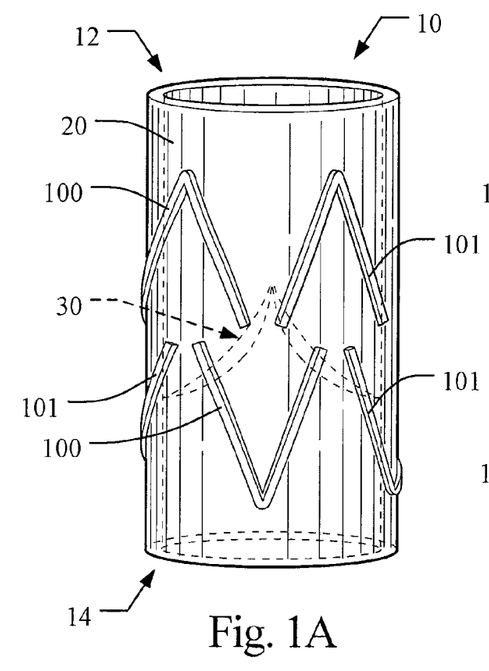
FIGS. 1A, 1B, and 1C depict illustrative examples of discrete shaping members.

In one aspect, shown in FIG. 1A for example, a prosthetic valve 10 comprising a flexible covering 20, discrete shaping members 100 and a valve member 30 can be used to regulate fluid flow in a vein, for example to treat venous valve incompetency. For example, the prosthetic valve 10 may comprise an expandable prosthesis having radially compressed and radially expanded configurations, allowing the valve member 30 to be delivered to and deployed at a point of treatment within a body vessel using percutaneous techniques and devices, the prosthetic valve 10 having a first or proximal end 12 and a second or distal end 14, with the normal, antegrade fluid flow typically traveling from the distal end 14 to the proximal end 12 of the device 10, the latter being located closest to the heart when placed within a body vessel. The discrete shaping members 100 may move relative to one another along the exterior surface of or within the flexible covering 20, or toward the center of the lumen defined within the tubular flexible covering 20 independent of one another. This may beneficially permit the prosthetic valve to comply with changes in the size and shape of a body vessel.

Flexible Covering

A wide variety of materials are acceptable for use as flexible covering material in implantable medical devices, and any suitable material can be utilized. The flexible covering 20 is preferably a remodelable material and is biocompatible, or able to be made biocompatible.

For example, a flexible covering may include a film, a coating, a sheet of biocompatible fabrics, non-woven materials or porous materials. Examples of biocompatible polymers from which a flexible covering can be formed include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include polymerization of biocompatible polymers from the material surface, coating of the surface with a crosslinked biocompatible polymer, and chemical modification with biocompatible functional groups. Thus, any polymer that may be formed into a porous sheet can be used to make a flexible covering, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above.

The flexible covering 20 may comprise biocompatible polyurethane. One example of a biocompatible polyurethane, THORALON (THORATEC, Pleasanton, Calif.), has been used in certain vascular applications and is characterized by thromboresistance, high tensile strength, low water absorption, low critical surface tension and good flex life. A variety of other biocompatible polyurethanes/polycarbamates and urea linkages (hereinafter "—C(O)N or CON type polymers") may also be employed. Biocompatible CON type polymers modified with cationic, anionic and aliphatic side chains may also be used. See, for example, U.S. Pat. No. 5,017,664, which is incorporated herein by reference in its entirety. Other biocompatible CON type polymers include: segmented polyurethanes, such as BIOSPAN; polycarbonate urethanes, such as BIONATE; polyetherurethanes, such as ELASTHANE; (all available from POLYMER TECHNOLOGY GROUP, Berkeley, Calif.); siloxane-polyurethanes, such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes, such as PURSIL-10, -20, and -40 TSPU; PTMO and PDMS polyether-based aliphatic siloxane-polyurethanes, such as PURSIL AL-5 and AL-10 TSPU; aliphatic, hydroxy-terminated polycarbonate and PDMS polycarbonate-based siloxane-polyurethanes, such as CARBOSIL-10, -20, and -40 TSPU (all available from POLYMER TECHNOLOGY GROUP). Examples of siloxane-polyurethanes are disclosed in U.S. Pat. Application Publication No. 2002/0187288 A1, which is incorporated herein by reference in its entirety.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference in its entirety.

The flexible covering 20 may also comprise extracellular matrix material (ECM). The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium or other tissues. One specific example of ECM is small intestine submucose (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts.

In addition to xenogenic biomaterials, such as SIS, autologous tissue can be harvested as well. Additionally Elastin or Elastin Like Polypetides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

Discrete Shaping Members

In one aspect, a prosthetic valve may comprise discrete shaping members (e.g., 100, 110, 120) attached to a flexible covering. As used herein, "discrete" means that the shaping members are not physically connected to one another. Preferably, the discrete shaping members are not in contact with one another, allowing the discrete shaping members to radially compress independent of one another. For example, upon implantation into a vessel, one or more discrete shaping members may radially compress due to vessel dynamics, while the remaining discrete shaping members remain unaffected. This may reduce inflammation, irritation, and thrombus formation within the vessel.

In one particular example, a prosthetic valve having discrete shaping members may be implanted in a vein. Veins are highly dynamic, and often fluctuate between flat, elliptical, circular, or other configurations. The ability of discrete shaping members to independently radially compress allows the prosthetic valve to better adapt and approximate the vein wall's configuration, and thus minimize possible irritation or inflammation. While annular or circumferential support members are commonly used in prosthesis implanted in arteries, such as a thoracic aorta, to seal an aneurysm or other portion of the artery from fluid flow, sealing is not critical to prosthetic valves implanted in veins.

The discrete shaping members may be attached to the flexible covering in any suitable manner. For example, the discrete shaping members may be attached to the flexible covering by sutures. The discrete shaping members may also be affixed to the flexible covering by dipping the discrete shaping members in a liquefied polymer and allowing the polymer to solidify into a flexible covering.

For example, discrete shaping members may be affixed to the flexible covering by coating a mandrel by dipping or spraying. In one example, a layer of polymer is deposited on a mandrel, for example by dipping and/or spraying, and permitted to solidify. The mandrel is preferably in the shape of the flexible covering to be formed. Discrete shaping members are then positioned over the first layer of polymer. A second layer of polymer is subsequently deposited, for example by dipping and/or spraying, on at least a portion of the discrete shaping members, the discrete shaping members being between the two polymeric layers that create the flexible covering. Alternatively, discrete shaping members may be sandwiched between two covering layers that may be bonded together, for example by vacuum pressing, heat welding (e.g., laser), and cross-linking.

Discrete shaping members permit the prosthesis to exhibit low radial force and high radial compressibility. Discrete shaping members may provide a certain rigidity and shape to the prosthesis without imparting a radial force similar to that of a stent. Low radial force mitigates undesirable physiological responses, such as vessel wall inflammation and thrombosis formation, and permits the medical device to exhibit dynamic movement. "Dynamic movement" refers to movement in response to external forces, such as changes in the dimensions of the lumen of the body vessel. Particularly preferred examples provide prosthetic valves comprising discrete shaping members responsive to dynamic movement by the interior of the body vessel. For example, the discrete shaping members permit the prosthesis to readily change from an elliptical to a circular cross-section in response to corresponding changes in the cross-section of a body vessel lumen. Preferably, the discrete shaping members allow a portion of the prosthesis to radially compress independent of the remaining prosthesis. For example, in FIG. 1A, discrete shaping members 100 may be radially compressed independent of remaining discrete shaping members 101. The ability of the discrete shaping members to move independently of one another may reduce inflammation, irritation, and thrombus formation in the vessel post-implantation as opposed to circumferential support members.

The discrete shaping members can have any suitable configuration and size. Preferably, the discrete shaping members do not extend circumferentially around a tubular flexible covering, but are separately attached to the flexible covering in a manner permitting the shaping members to move circumferentially with respect to one another by radially expanding or compressing the tubular flexible covering. For example, in one aspect, the shaping members are not annular or circumferential members. The exact configuration and size chosen will depend on several factors, including the desired delivery technique, the nature of the body vessel in which the valve will be implanted, and the size of the vessel. The discrete shaping members are preferably shaped to maintain a prosthetic valve in a desired configuration or orientation within a body vessel. For example, the discrete shaping members can be sized so that the second, expanded configuration is slightly larger in diameter that the inner diameter of the vessel in which the prosthetic valve will be implanted. This sizing can facilitate anchoring of the prosthetic valve within the body lumen and maintenance of the prosthetic valve at a point of treatment following implantation.

Figure 1B:
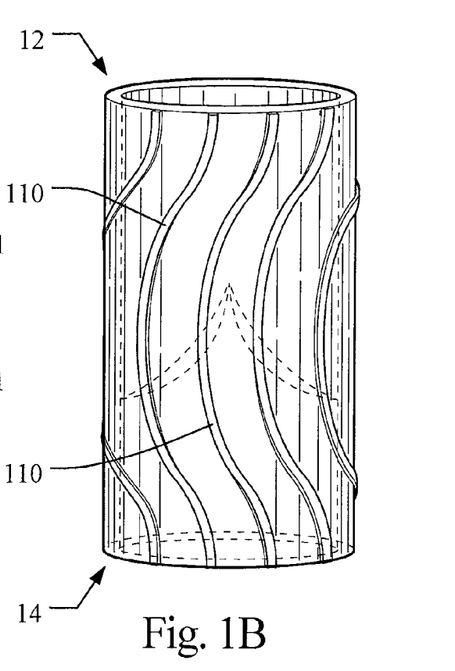
Figure 1C:
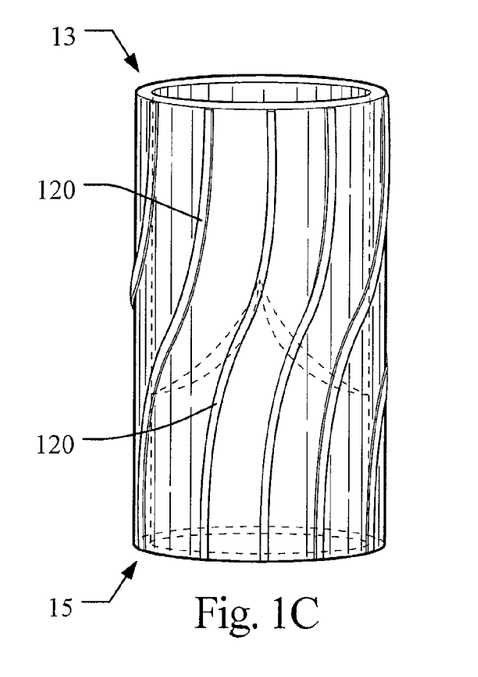

In one aspect, the discrete shaping members comprise a plurality of discrete struts and bends, which can be of any suitable structure or orientation. For example, FIG. 1A shows discrete shaping members comprising a plurality of discrete Z-stent segments 100. FIG. 1B illustrates discrete shaping members comprising a plurality of discrete struts having a curvilinear form 110, being substantially parallel to the longitudinal axis of the prosthesis, and extending from the prosthetic valve's proximal end 12 to the distal device end 14. FIG. 1C depicts discrete shaping members comprising a plurality of discrete struts having a sinusoidal form 120, being substantially parallel to the longitudinal axis of the prosthesis, extending from the prosthetic valve's proximal end 13 to the distal device end 15.

In one aspect, the discrete shaping members are configured to form an artificial sinus 40 adjacent to and surrounding the valve member 31 when the device 11 is deployed within a body vessel, such as a vein of the lower legs. It is believed that the rounded shape of the enlarged artificial sinus 40 acts to prevent blood from pooling or stagnating about the base of the valve member 31, which may lead to thrombus formation or other problematic conditions.

For example, in one aspect, discrete shaping members 200 may form a sinus 40 in response to pressure variations in the venous system. The discrete shaping members 200, when combined with an increase in venous system blood pressure, will define a sinus 40 within a lumen defined by the flexible covering 21 and surrounding the valve member 31. During a decrease in venous system blood pressure, the sinus 40 may at least slightly abate as the discrete shaping members 200 do not exhibit sufficient radial force alone to form a sinus.

In one aspect, the plurality of discrete shaping members 200 move circumferentially along the exterior surface of or within the flexible covering 21 at a given position along the longitudinal axis within the lumen of the tubular flexible covering 21. Preferably, when the prosthetic valve device is expanded from the radially compressed configuration to the radially expanded configuration, the discrete shaping members 200 move relative to one another. Such movement preferably does not occur within a single unbroken annular sinusoidal ring member, where portions of a single annular shaping member move relative to one another at a given position along the longitudinal axis.

Figure 2A:
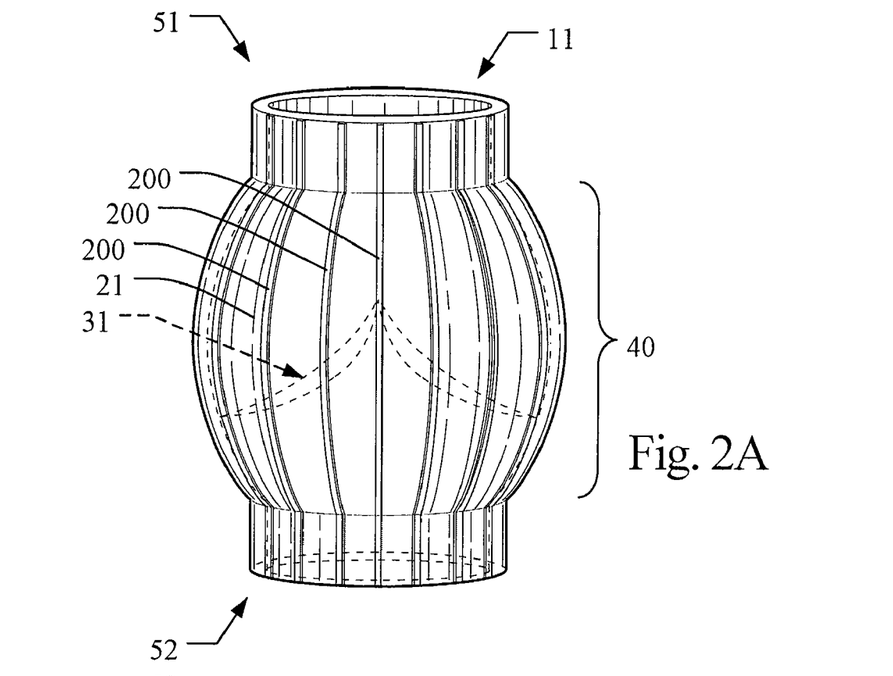
FIGS. 2A, 2B and 2C depict illustrative examples of discrete shaping members capable of forming a sinus.
Figure 2B:
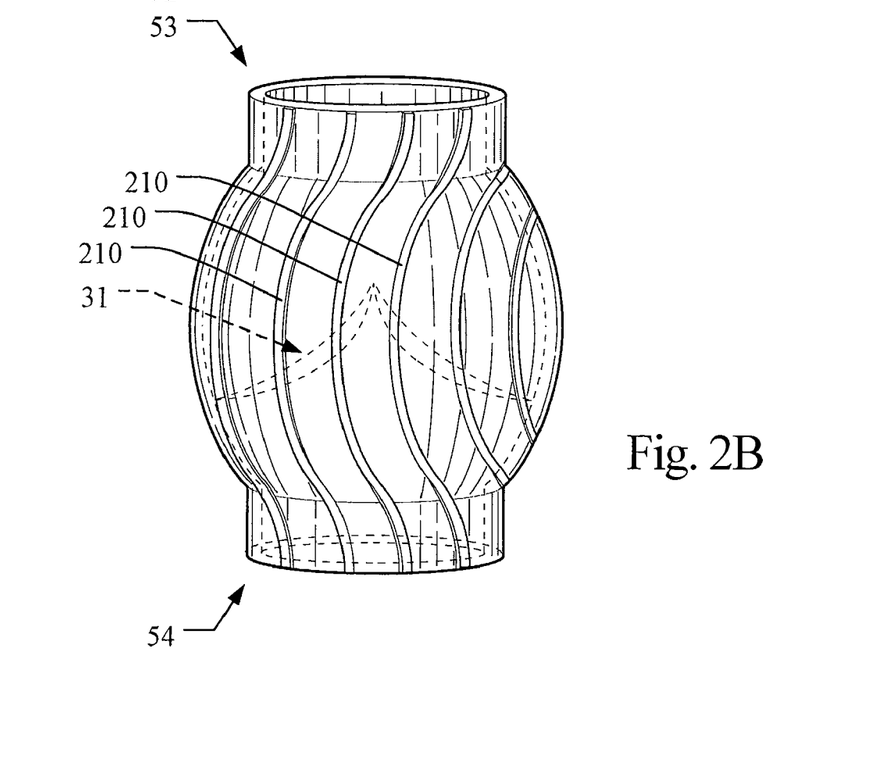
Figure 2C:
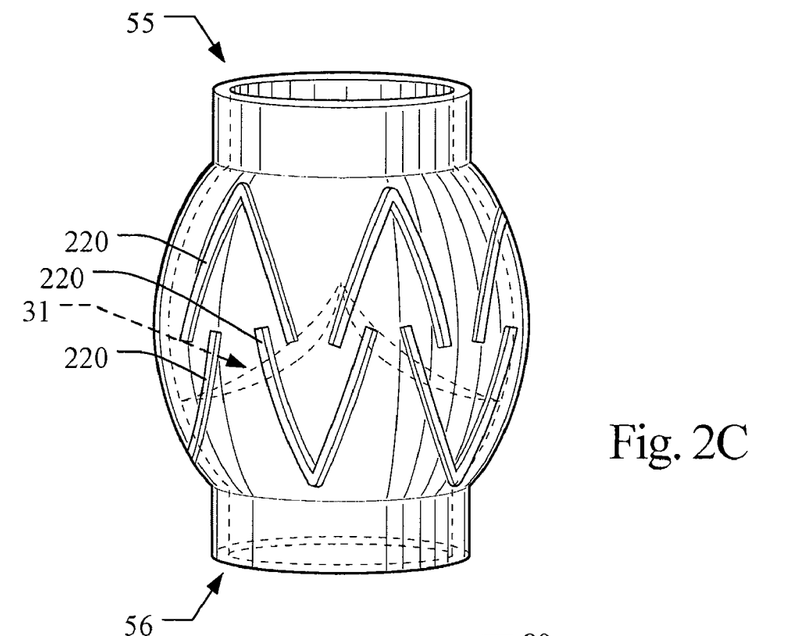

FIGS. 2A, 2B, and 2C illustrate discrete shaping members configured to form a sinus about the valve member 31. FIG. 2A shows discrete shaping members comprising a plurality of discrete, longitudinal struts 200, being substantially parallel to the longitudinal axis of the prosthesis, extending from the prosthetic valve's proximal end 51 to the distal device end 52. FIG. 2B illustrates discrete shaping members comprising a plurality of discrete struts having a curvilinear form 210, being substantially parallel to the longitudinal axis of the prosthesis, extending from the prosthetic valve's proximal end 53 to the distal device end 54. FIG. 2C shows discrete shaping members comprising a plurality of discontinuous bowed Z-stent segments 220 located substantially intermediate the device proximal 55 and distal 56 ends. The longitudinal struts 200, curvilinear struts 210, and discontinuous bowed Z-stent segments 220 create an artificial sinus around the valve member with minimal radial force. In one example, the prosthetic valve shown in FIG. 1C may be radially expanded to form the prosthetic valve 10 shown in FIG. 2B, thereby changing the shape of the shaping members 120 to form the shaping members 210 and urging shaping members (120, 210) to move relative to one another during the expansion.

It should be understood that the materials used to comprise the discrete shaping members need only be biocompatible or able to be made biocompatible. Examples of suitable materials include, without limitation, stainless steel, nitinol, MP35N, gold, tantalum, platinum or platinum irdium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, styrene isobutylene-styrene block copolymer (Kraton), polyethylene teraphthalate, polyurethane, polyamide, polyester, polyorthoester, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin, or combinations thereof. Desirably, the discrete shaping members comprise stainless steel or nitinol.

Also provided are aspects wherein at least one discrete shaping member comprises a means for orienting the prosthetic valve within a body lumen. For example, a discrete shaping member can comprise a marker, such as a radiopaque portion of the shaping member that would be seen by remote imaging methods including X-ray, ultrasound, Magnetic Resonance Imaging and the like, or by detecting a signal from or corresponding to the marker. In other aspects, the delivery device can comprise a frame with indicia relating to the orientation of the prosthetic valve within the body vessel. In other aspects, indicia can be located, for example, on a portion of a delivery catheter that can be correlated to the location of the prosthetic valve within a body vessel. The discrete shaping members or delivery device may comprise one or more radiopaque materials to facilitate tracking and positioning of the medical device, which may be added in any fabrication method or absorbed into or sprayed onto the surface of part or all of the prosthetic valve. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platium, iridium, and rhodium. In one preferred embodiment, iodine may be employed for its radiopacity and antimicrobial properties. Radiopacity is typically determined by fluoroscope or x-ray film.

Attachment of Prosthetic Valve in Body Vessel

In one aspect, a prosthetic valve may optionally include supplemental attachment means such as anchoring devices, proximal or distal stents, suturing, stapling, searing, bonding, gluing, or otherwise adhering the medical device to the vessel wall or combinations thereof. For example, the prosthetic valve may be secured in place with one or more anchoring devices.

A wide variety of structural features are acceptable for use in medical devices as anchoring devices, and any suitable structural feature can be used. For example, individual barbs may be used to implant the prosthetic valve into the vessel. The barbs may be secured to the prosthetic valve by any means known to one skilled in the art, including but not limited to welding, stitching, bonding, and adhesives. Furthermore, barbs can also comprise separate members attached to the prosthetic valve by suitable attachment means.

Figure 3A:
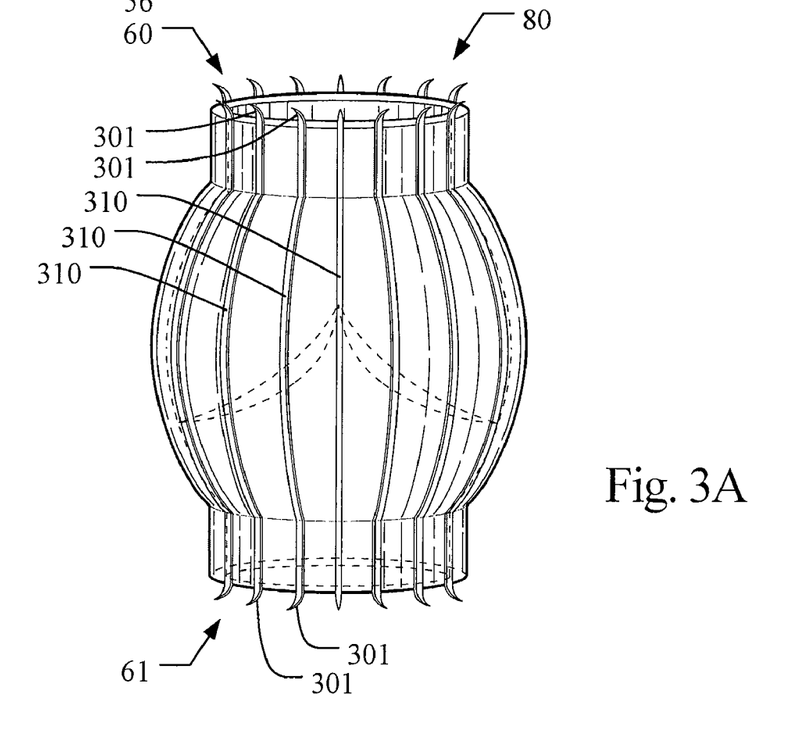
FIGS. 3A, 3B, 3C and 3D depict illustrative examples in which the prosthesis includes anchoring devices.

In one aspect, the discrete shaping members may comprise features, such as barbs, that maintain the prosthetic valve in position following implantation in a body vessel. FIGS. 3A, 3B, 3C and 3D illustrate exemplary embodiments of the support frame comprising barbs to facilitate maintenance of the device in the body vessel. FIG. 3A illustrates prosthetic valve 80 comprising discrete longitudinal struts 310 having an arcuate configuration with barbs 301 located at the distal 61 and proximal 60 ends of the prosthetic valve 80. Preferably, barbs 301 comprise the proximal and distal ends of discrete struts 310, the ends formed to extend outward from the flexible covering material to form barbs 301.

Figure 3B:
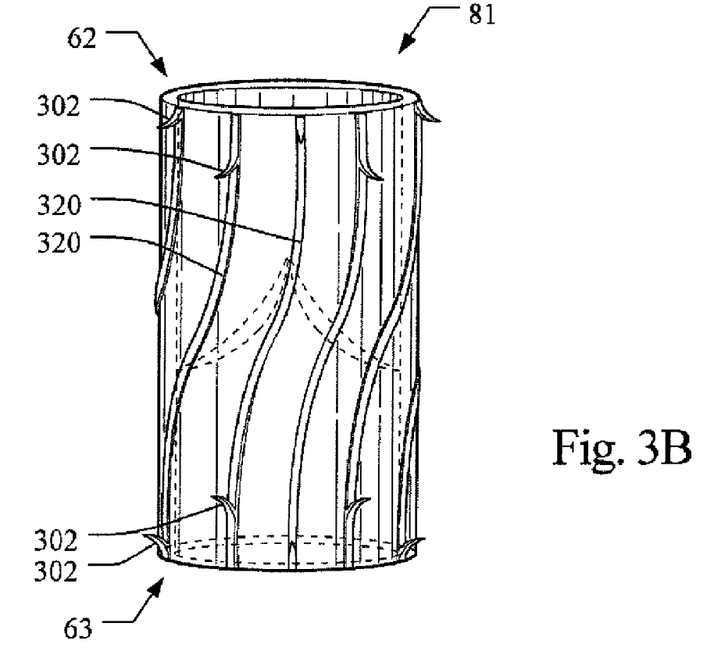

FIG. 3B depicts prosthetic valve 81 comprising a plurality of discrete struts having a sinusoidal form 320 with barbs 302 located at the distal 63 and proximal 62 ends of the prosthetic valve 81. Barbs 302 aid in securing the prosthetic valve 81 in the body vessel following implantation.

Figure 3C:
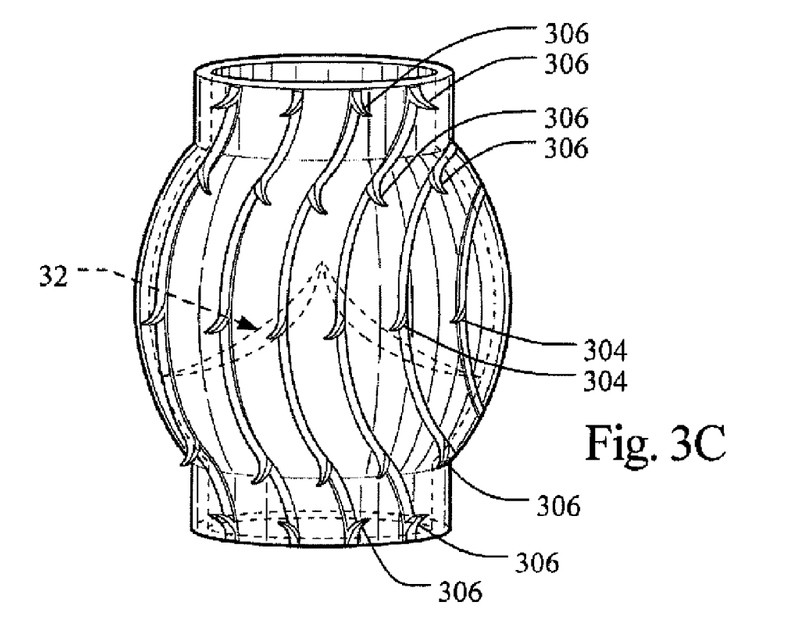
Figure 3D:
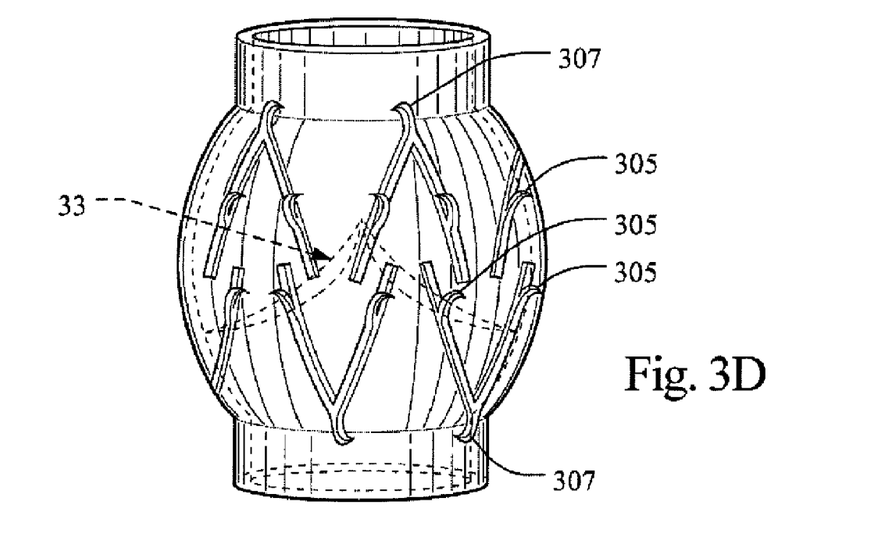

FIGS. 3C and 3D depict prosthetic valves with barbs 304, 305 located substantially about the valve member 32, 33 in addition to barbs 306, 307. Similar to FIG. 3B, barbs 306, 307 aid in securing the medical device in the body vessel following implantation. Barbs 304, 305 further secure the region surrounding valve member 32, 33 to the vessel wall.

In some aspects, the number, arrangement, and configuration of the integral barbs can vary according to design preference and the clinical use of the device. The barbs can have any suitable shape, including points or "fish hook"-like configurations. The barbs may or may not penetrate the vein wall, depending on their design and other factors, including the thickness and type of flexible covering used.

Alternatively or in addition to anchoring devices, bioadhesives may be used for attachment. The bioadhesive can be included in any suitable part of the prosthetic valve. In one aspect, the bioadhesive is attached to the abluminal surface of the flexible covering. Selection of the type of bioadhesive, the portions of the prosthetic valve comprising the bioadhesive, and the manner of attaching the bioadhesive to the prosthetic valve can be chosen to perform a desired function upon implantation. For example, the bioadhesive can be selected to promote increased affinity of the desired portion of prosthetic valve to the section of the body vessel against which it is urged.

Bioadhesives for use in conjunction with the present disclosure include any suitable bioadhesives. For example, appropriate bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta(TGF-B); (4) polysaccharides such as acacia, carboxymethyl-cellulose, dextran, hyaluronic acid, hydroxypropyl-cellulose, hydroxypropyl-methylcellulose, karaya gum, pectin, starch, alginates, and tragacanth; (5) polyacrylic acid, polycarbophil, modified hypromellose, gelatin, polyvinylpylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivitized with sticky molecules such as arginine, glycine, and aspartic acid, and copolymers.

In one example, the bioadhesive may be curable by light. For example, light curable adhesives suitable for medical devices are disclosed in U.S. Publication No. 2008/0004686 to James Hunt et al. for IMPLANTABLE DEVICE WITH LIGHT-TRANSMITTING MATERIAL, which is herein incorporated by reference. Furthermore, commercially available bioadhesives that may be used in the present invention include, but are not limited to: FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Alternatively or in addition to bioadhesives and anchoring devices, the medical device may optionally be anchored by applying energy to the prosthetic valve. Energy may be applied to the prosthetic device by any suitable method. For example, an energy delivery device may be configured to deliver one or more different types of energy to the prosthetic valve during deployment including, but not limited to, electromagnetic radiation (RF, microwave, ultraviolet, visible light, laser), ultrasound, resistive heating, frictional heating, and electricity. In one aspect, electrical current and/or heat may be applied to at least one discrete shaping member to secure the device within the body vessel, for example by melting a portion of the device or heat activating a bioadhesive included in the prosthetic valve. Energy applied to at least one discrete shaping member may also cauterize local tissue upon impantation to aid device fixation. In one example, the electrical energy applied to the discrete shaping members is between about 0.01 to about 10.0 milliamps at about 0.1 to about 10.0 volts.

Optionally, to facilitate maintenance of the device in the vessel following implantation and aid in directing fluid flow through the prosthetic valve lumen, the prosthetic valve may comprise additional reinforcing means about the distal and proximal portions of the prosthetic valve. For example, the flexible covering may be made thicker about the proximal and distal ends, such as an SIS cuff, to provide reinforcement to the prosthetic valve proximal and distal ends. Alternatively, stents may be located about the distal and proximal portions of the flexible covering to secure the device and aid in directing fluid flow.

Figure 4A:
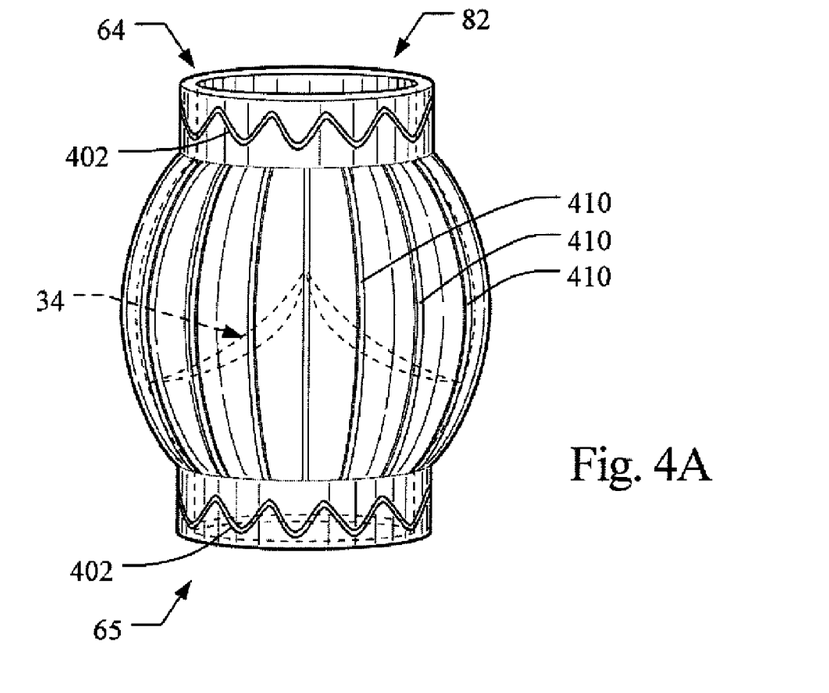
FIGS. 4A, 4B, and 4C depict illustrative examples in which the prosthesis includes stents about the proximal and distal prosthesis sections.
Figure 4B:
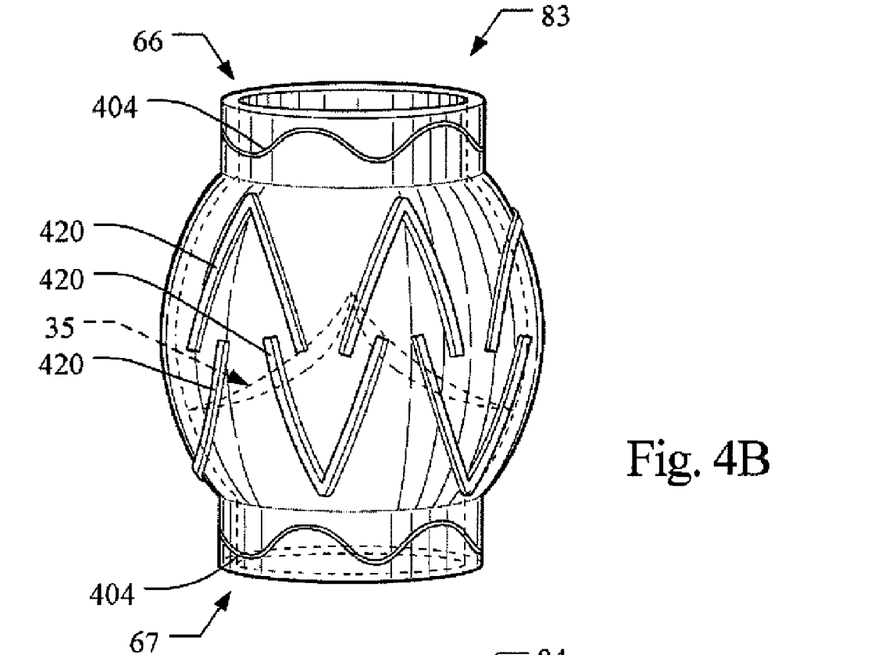
Figure 4C:
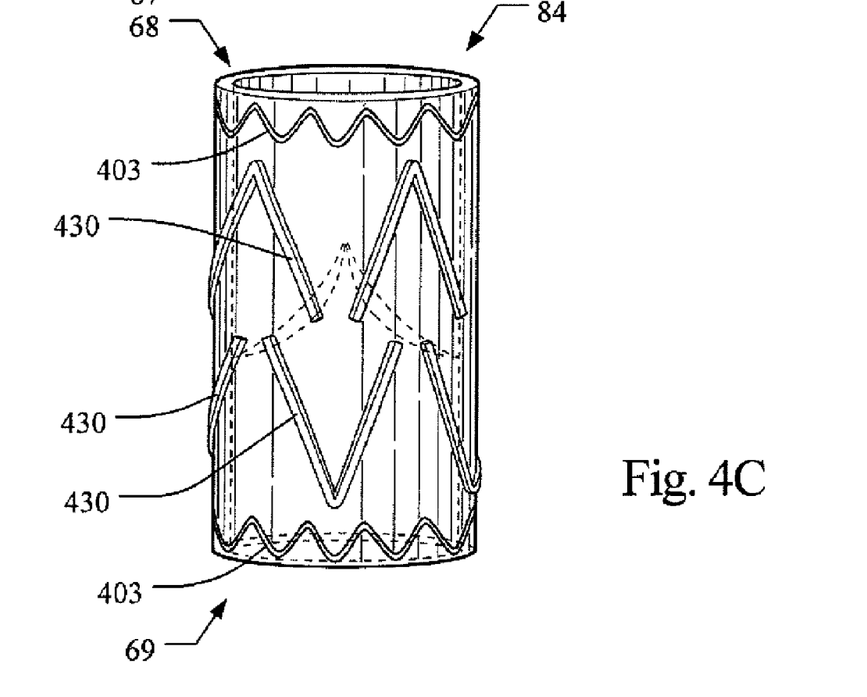

FIGS. 4A, 4B, and 4C illustrate examples comprising circumferential radially expandable stents located at the medical device's proximal and distal ends to facilitate device maintenance following implantation. FIG. 4A illustrates discrete shaping members comprising discrete longitudinal struts 410 about valve member 34 and circumferential Z-stents 402 about the distal 65 and proximal 64 ends of the prosthetic valve 82. FIG. 4B illustrates discrete shaping members comprising discrete Z-stent segments 420 about valve member 35 and circumferential curvilinear stents 404 at the proximal 66 and distal 67 ends of the prosthetic valve 83. FIG. 4C depicts discrete shaping members comprising a plurality of discrete Z-stent segments 430 and circumferential Z-stents 403 about the distal 69 and proximal 68 ends of the prosthetic valve 84. The circumferential expandable stents 402, 403 and 404 exhibit a radial force sufficient to securely maintain the device in the body vessel following implantation.

Valve Members

Prosthetic valves may comprise at least one valve member attached to the prosthetic valve. Prosthetic valves comprising at least one valve member can be used to regulate fluid flow in a vein, for example, to treat venous valve incompetency. For example, one or more prosthetic valves comprising one or more valve members can be implanted in a vein with incompetent native venous valves so as to provide a valve to replace the incompetent native valves therein.

A valve member, according to some aspects, can comprise a leaflet comprising a free edge responsive to the flow of fluid through the body vessel. A "free edge" refers to a portion of a leaflet that is not attached to the prosthetic valve, but forms a portion of a valve orifice. Preferably a leaflet free edge is a portion of the edge of the leaflet that is free to move in response to the direction of fluid flow in contact with the leaflet. A valve leaflet is one type of valve member. Other suitable valve member configurations may also be used, for example a tubular valve or other non-leaflet valve configuration. Preferably, one or more valve members attached to a prosthetic valve can permit fluid to flow through a body vessel in a first direction while substantially preventing fluid flow in the opposite direction.

A wide variety of materials acceptable for use as valve members are known in the art, and any suitable material can be utilized. The material chosen need only be able to perform as described herein, and be biocompatible, or able to be made biocompatible. Examples of suitable materials include flexible materials, natural materials, and synthetic materials. Examples of suitable natural materials include collagen and extracellular matrix (ECM) material, such as submucosa. Small intestine submucosa (SIS) is particularly well-suited for use as valve members, such as leaflets. Examples of suitable polymeric materials include polyesters, such as poly (ethylene terephthalate); fluorinated polymers, such as polytetrafluoroethylene (PTFE), expanded PTFE and poly (vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, and chemical modification with biocompatible functional groups.

Desirably, the valve member is made of one or more polymers that do not require treatment or modification to be biocompatible. More desirably, the valve member includes a biocompatible polyurethane. Examples of biocompatible polyurethanes include, but are not limited to, polycarbonate urethanes, such as BIONATE; polyetherurethanes, such as ELASTHANE; (all available from POLYMER TECHNOLOGY GROUP, Berkeley, Calif.); siloxane-polyurethanes, such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes, such as PURSIL-10, -20, and -40 TSPU; PTMO and PDMS polyether-based aliphatic siloxane-polyurethanes, such as PURSIL AL-5 and AL-10 TSPU; aliphatic, hydroxy-terminated polycarbonate and PDMS polycarbonate-based siloxane-polyurethanes, such as CARBOSIL-10, -20, and -40 TSPU (all available from POLYMER TECHNOLOGY GROUP).

A valve member may be applied to the prosthetic valve with any suitable attachment mechanism, such as sutures, dipping, adhesives, bonding, tissue welding, self-adhesion between regions of the material, chemical adhesion between the valve member and frame, spraying, cross-linking, and the like. The attachment mechanism chosen will depend on the nature of the frame and valve members. For example, in one aspect, the biocompatible polyurethane may be applied as a solution. If necessary, gentle heating and/or agitation, such as stirring, may be employed to cause substantial dissolution.

Although the prosthetic valves in the illustrative figures are shown with valve members having one or two valve leaflets, the valve member may include any suitable number of leaflets. The valve member need only be able to provide the functionality described herein. The specific number chosen will depend on several factors, including the type and configuration of the frame. For example, the valve member may comprise 1, 2, 3, 4, 5, 6, 7, 8, or more leaflets. The leaflets can be arranged in any suitable configuration with respect to one another and the prosthetic valve.

Figure 5A:
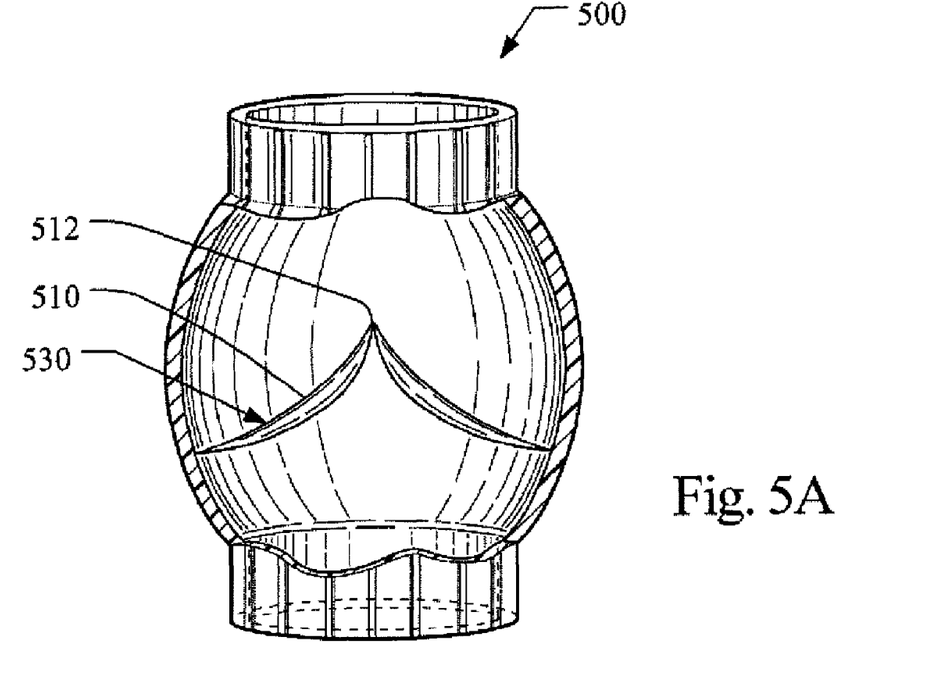
FIGS. 5A, 5B, 5C, and 5D depict cut-aways of illustrative examples of prosthesis valve members.
Figure 5B:
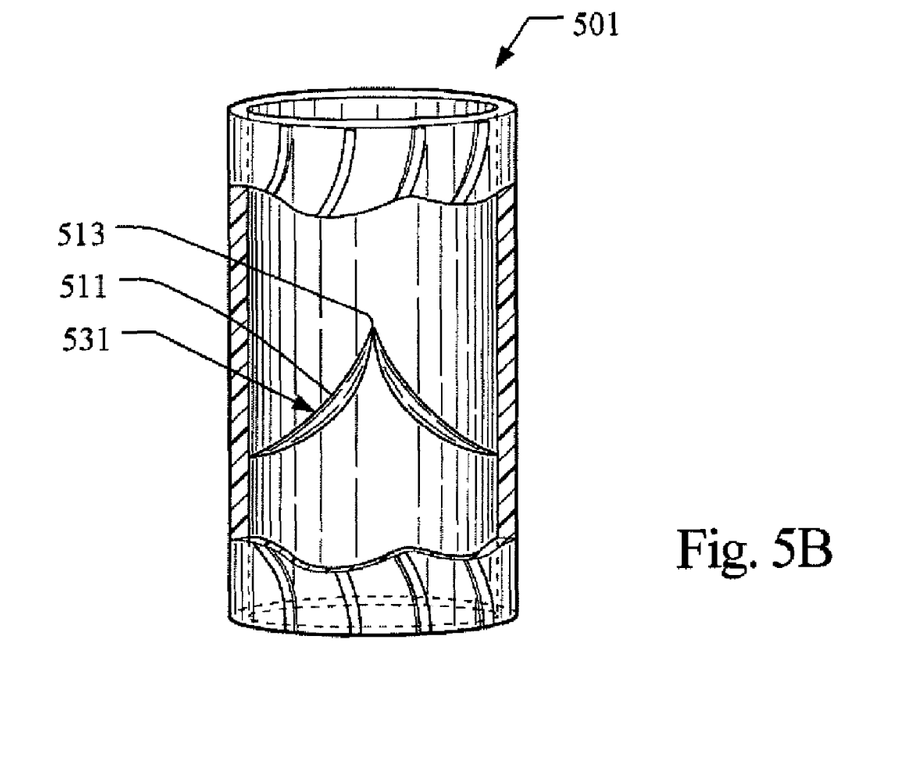
Figure 5C:
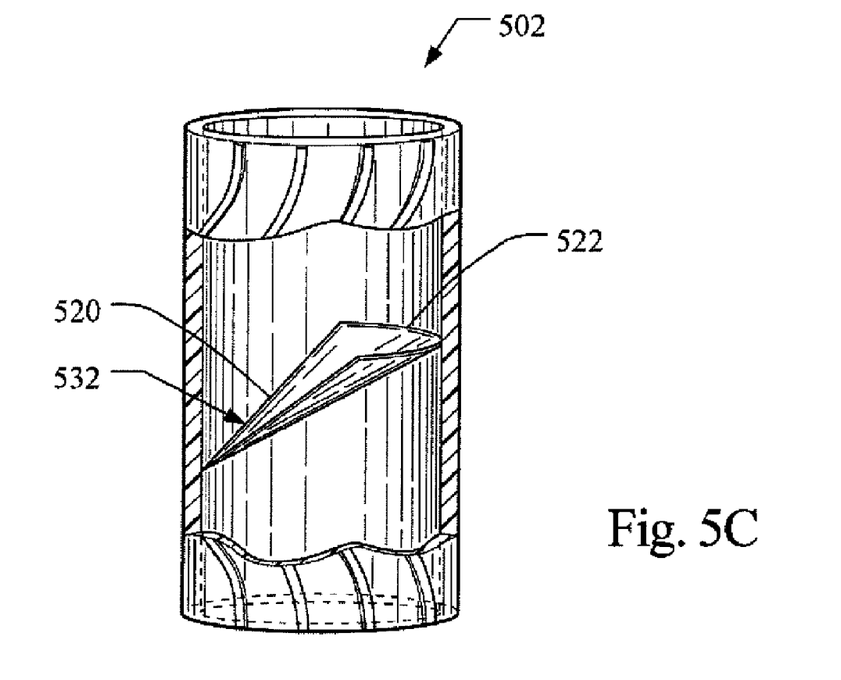
Figure 5D:
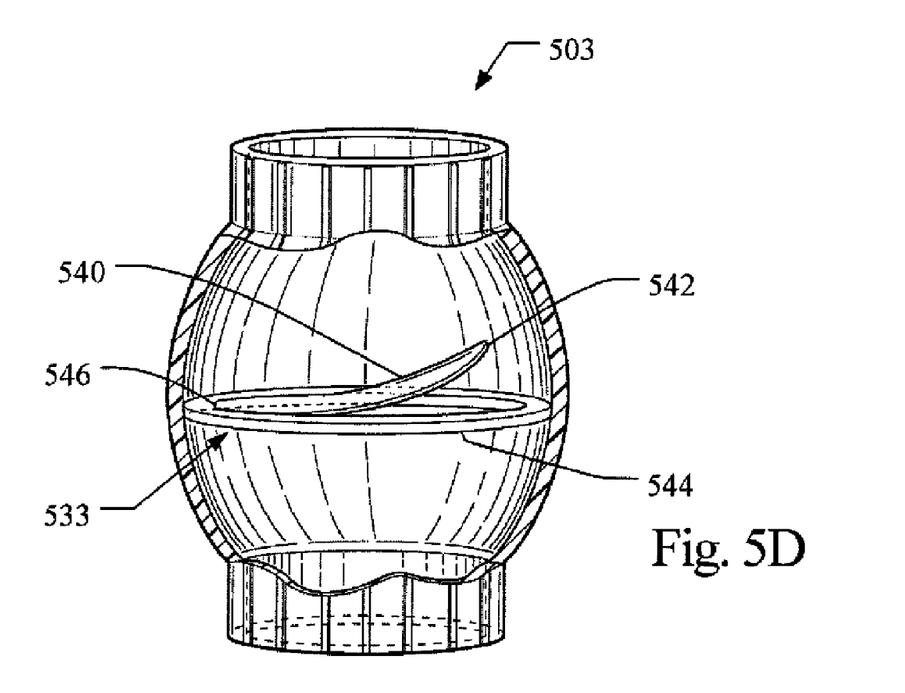

In one aspect, a valve member can comprise two valve leaflets comprising free edges that may coapt with one another. FIGS. 5A and 5B show a cut-away of prosthesis 500, 501 in which the valve member 530, 531 comprises two valve leaflets 510, 511 as a means for regulating flow. Each leaflet 510, 511 has a free edge 512, 513, which cooperatively defines the valve orifice. In another aspect, a prosthetic valve can comprise one leaflet having a free edge that can sealably engage the device luminal wall. FIG. 5C illustrates a cut-away of prosthetic valve 502 in which the valve member 532 has a single leaflet 520 with a free edge 522. FIG. 5D depicts a cut-away of an alternative embodiment of prosthesis 503 where the valve member 533 comprises a single leaflet 540 with free edge 542. The leaflet 540 is mounted within a housing 544 and is operatively connected to the housing 544 via a hinge 546 allowing the leaflet 540 to freely move in response to flow. In yet a further aspect, the valve member may comprise three valve leaflets.

Bioactive Agents

Optionally, the prosthetic valve can include one or more bioactive agents. The bioactive agent can be included in any suitable part of the prosthetic valve. Selection of the type of bioactive agent, the portions of the prosthetic valve comprising the bioactive agent, and the manner of attaching the bioactive agent to the prosthetic valve can be chosen to perform a desired function upon implantation. For example, the bioactive material can be selected to treat indications such as coronary artery angioplasty, renal artery angioplasty, carotid artery surgery, renal dialysis fistulae stenosis, or vascular graft stenosis.

The bioactive materials can be attached to the prosthetic valve in any suitable manner. For example, a bioactive agent can be combined with a biocompatible polyurethane, impregnated in the valve members, positioned within or on the flexible covering, or attached to the surface of the prosthetic valve.

The bioactive agent can be selected to perform one or more desired biological functions. For example, the abluminal surface of the flexible covering can comprise a bioactive agent selected to promote the ingrowth of tissue from the interior wall of a body vessel, such as a growth factor. An antiangiogenic or antineoplastic bioactive agent such as paclitaxel, sirolimus, or a rapamycin analog, or a metalloproteinase inhibitor such as batimastaat can be incorporated in or coated on the discrete shaping members or flexible covering to mitigate or prevent undesired conditions in the vessel wall, such as restenosis. Many other types of bioactive agents can be incorporated in the prosthetic valve.

Bioactive materials for use in biocompatible coatings include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, antiangiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

Prosthetic valves comprising an antithrombogenic bioactive agent are particularly preferred for implantation in areas of the body that contact blood. For example, an antithromogenic bioactive agent can be coated on the valve member surface. An antithrombogenic bioactive agent is any bioactive agent that inhibits or prevents thrombus formation within a body vessel. The prosthetic valve can comprise any suitable antithrombogenic bioactive agent. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Also preferred are prosthetic valves comprising a thrombolytic bioactive agent. In one example, the thrombolytic bioactive agent is positioned on the luminal surface of the flexible covering or within the valve members. Thrombolytic agents are used to dissolve blood clots that may adversely affect blood flow in body vessels. A thrombolytic agent is any therapeutic agent that either digests fibrin fibres directly or activates the natural mechanisms for doing so. The medical device can comprise any suitable thrombolytic agent. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA.

A bioactive agent can be incorporated in or applied to portions of the prosthetic valve by any suitable method that permits adequate retention of the bioactive agent material and the effectiveness thereof for an intended purpose upon implantation in the body vessel. The configuration of the bioactive agent on or in the prosthetic valve will depend in part on the desired rate of elution for the bioactive agents. Bioactive agents can be coated directly on the prosthetic valve surface or can be adhered to a prosthetic valve surface by means of a coating. For example, an antithrombotic bioactive agent can be blended with a polymer and spray or dip coated on the device surface. For example, a bioactive agent material can be posited on the surface of the prosthetic valve and a porous coating layer can be posited over the bioactive agent material. The bioactive agent material can diffuse through the porous coating layer. The coating layer can also be nonporous wherein the rate of diffusion of the bioactive agent material through the coating layer is controlled by the rate of dissolution of the bioactive agent material in the coating layer.

Delivery of Prosthetic Valves

The prosthetic valves of the present invention can be configured for delivery to a body vessel. For example, a prosthetic valve can be compressed to a delivery configuration within a retaining sheath that is part of a delivery system, such as a catheter-based system. Upon delivery, the prosthetic valve can be expanded, for example, by inflating a balloon from inside the prosthetic valve. The delivery configuration can be maintained prior to deployment of the prosthetic valve by any suitable means, including a sheath, a suture, a tube or other restraining material around all or part of the compressed prosthetic valve, or other methods.

Prosthetic valves can be deployed in a body lumen by any means appropriate to their design. The prosthetic valves of the present invention can be adapted for deployment using conventional methods known in the art and employing percutaneous transluminal catheter devices. The prosthetic valves are designed for deployment by any of a variety of in situ expansion means.

For example, in one aspect, the flexible covering lumen of the prosthetic valve may first positioned to surround a portion of an inflatable balloon catheter. The prosthetic valve, with the balloon catheter inside is configured at a first, collapsed diameter. The prosthetic valve and the inflatable balloon are percutaneously introduced into a body lumen, following a previously positioned guidewire, for example in an over-the-wire angioplasty catheter system or rapid exchange delivery, and tracked by a fluoroscope, until the balloon portion and associated prosthetic valve are positioned within the body passageway at the point where the prosthetic valve is to be placed. Thereafter, the balloon is inflated and the prosthetic valve is expanded by the balloon portion from the collapsed diameter to a second expanded diameter. After the prosthetic valve has been expanded to the desired final expanded diameter, the balloon is deflated and the catheter is withdrawn, leaving the prosthetic valve in place. The prosthetic valve may be covered by a removable sheath during delivery to protect both the prosthetic valve and the vessels.

The medical devices described herein can be placed in any medically appropriate location for a given application. For example, in some examples, the medical device can serve as part of a venous valve prosthetic and be implanted in the femoral vein, including at the proximal (groin), mid (mid section) or distal (adjacent to the knee) portions of the vein. The medical device can be preferably implanted within the tibial arteries for treatment of critical limb ischemia (CLI). For instance, the medical device can be configured as a vascular stent having a self-expanding support frame formed from a superelastic self-expanding nickel-titanium alloy attached to a covering material. The use of a self-expanding frame can be preferably used when the body vessel to be stented extends into the distal popliteal segment. The selection of the type of implantable frame can also be informed by the possibility of external compression of an implant site within a body vessel during flexion of the leg.

While the terms "contracted" and "compressed" have been used to describe the prosthetic valve as having the small diameter necessary for delivery to an implantation site, it will be appreciated that the terms, especially as applied to pressure-expandable prosthetic valves, should not be used to imply that the tube is under external pressure to provide the tube with a small diameter; i.e., a "contracted" or "compressed" pressure-expandable prosthetic valve may be formed and naturally reside in the "contracted" or "compressed" state until internally pressurized to expand. Therefore, "contracted" and "compressed" are intended only to imply that the prosthetic valve is in a state of having a small diameter relative to an expanded state. It will, therefore, be appreciated by those skilled in the art that yet other modifications could be made to the provided invention without deviating from its spirit and scope as so claimed.

Methods for delivering a prosthetic valve as described herein to any suitable body vessel are also provided, such as a vein, artery, biliary duct, ureteral vessel, body passage or portion of the alimentary canal.

Methods of Treatment

Still other aspects provide methods of treating a subject, which can be animal or human, comprising the step of providing one or more prosthetic valves as described herein. In some aspects, methods of treatment may also provide the step of delivering a prosthetic valve to a point of treatment in a body vessel, or deploying a prosthetic valve at the point of treatment, wherein the prosthetic valves are as described herein.

The invention also provides methods of treating a patient. In one aspect the method comprises a step of delivering a prosthetic valve as described herein to a point of treatment in a body vessel, and deploying the prosthetic valve at the point of treatment. The delivering step can comprise delivery by surgical or by percutaneous delivery techniques known to those skilled in the art.

In a first aspect, methods of treating venous valve related conditions are provided. A "venous valve related condition" is any condition presenting symptoms that can be diagnostically associated with improper function of one or more venous valves. In mammalian veins, natural valves are positioned along the length of the vessel in the form of leaflets disposed annularly along the inside wall of the vein which open to permit blood flow toward the heart and close to prevent back flow. These natural venous valves act as open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve related conditions are chronic venous insufficiency and varicose veins. In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The varicose vein condition consists of dilatation and tortuousity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves. The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforation, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

In a second aspect, methods of treating peripheral vascular disease, including critical limb ischemia, are provided. Atherosclerosis underlies most peripheral vascular disease. Narrowed vessels that cannot supply sufficient blood flow to exercising leg muscles may cause claudication, which is brought on by exercise and relieved by rest. As vessel narrowing increases, critical limb ischemia (CLI) can develop when the blood flow does not meet the metabolic demands of tissue at rest. While critical limb ischemia may be due to an acute condition such as an embolus or thrombosis, most cases are the progressive result of a chronic condition, most commonly atherosclerosis. The development of chronic critical limb ischemia usually requires multiple sites of arterial obstruction that severely reduce blood flow to the tissues. Critical tissue ischemia can be manifested clinically as rest pain, nonhealing wounds (because of the increased metabolic requirements of wound healing) or tissue necrosis (gangrene).

Methods for treating other conditions are also provided, such as esophageal reflux, restenosis or atherosclerosis. In some aspects, the invention relates to methods of treating venous valve-related conditions.

While many examples discussed herein reference implantation of a prosthetic valve in a vein, other examples provide for implantation within other body vessels. In another matter of terminology there are many types of body canals, blood vessels, ducts, tubes and other body passages, and the term "vessel" is meant to include all such passages.

The invention includes other aspects within the scope of the claims, and variations of all aspects and examples, and is limited only by the claims made by the Applicants.

The invention claimed is:

1. A prosthetic valve for implantation in a body vessel having an expanded configuration and a compressed configuration, the prosthetic valve comprising:
    a flexible covering having a proximal covering end, a distal covering end, a luminal surface, an abluminal surface, and an axial length extending between the proximal covering end and distal covering end, the flexible covering defining an interior lumen, the flexible covering having a longitudinal axis extending between the proximal covering end and the distal covering end and a circumference extending around the abluminal surface;
    a plurality of discrete shaping members attached only to the flexible covering, each of the discrete shaping members comprising a discontinuous Z-stent segment having a V-shape with a first free end, a second free end, and an apex, each of the Z-stent segments extending only partially around the circumference of the flexible covering; and
    at least one valve member operatively connected to the luminal surface, the at least one valve member adapted to modify fluid flow through the interior lumen;
    wherein each of the first free end, second free end, and apex of each Z-stent segment is disposed on the flexible covering between the proximal covering end and the distal covering end.

2. The prosthetic valve of claim 1, where the flexible covering comprises a sinus.

3. The prosthetic valve of claim 1, where the plurality of discrete shaping members are adapted to move circumferentially relative to one another along the abluminal surface of the flexible covering when the prosthetic valve is moved between the compressed configuration and the expanded configuration.

4. The prosthetic valve of claim 1, further comprising a first stent attached near the proximal covering end and a second stent attached near the distal covering end.

5. The prosthetic valve of claim 1, where at least one discrete shaping member comprises an energy-sensitive material.

6. The prosthetic valve of claim 5, where the energy-sensitive material increases in temperature when an energy source is applied thereto, the energy source selected from the group consisting of radiofrequency energy, electrical energy, ultrasound energy, laser energy, microwave energy, and electromagnetic energy.

7. The prosthetic valve of claim 1, where the flexible covering abluminal surface comprises a bioadhesive.

8. The prosthetic valve of claim 7, where the bioadhesive comprises a bioadhesive curable by ultraviolet light exposure.

9. The prosthetic valve of claim 1, where the discrete shaping members are selected from the group consisting of stainless steel, nitinol, tantalum, a nonmagnetic nickel-cobalt-chromium-molybdenum alloy, platinum, titanium, a suitable biocompatible alloy, a suitable biocompatible polymer, a suitable biocompatible material, and a combination thereof.

10. The prosthetic valve of claim 1, where the flexible covering comprises a material selected from the group consisting of biocompatible polyurethane, polyethylene terephthlate, polytetrafluoroethylene, and extracellular matrix material.

11. The prosthetic valve of claim 1, where the prosthetic valve further comprises anchoring devices.

12. The prosthetic valve of claim 1, wherein each discrete shaping member consists of a discontinuous Z-stent segment consisting of a V-shape.

13. The prosthetic valve of claim 1, wherein each discontinuous Z-stent segment is bowed.

14. The prosthetic valve of claim 13, wherein the plurality of discrete shaping members creates an artificial sinus in the flexible covering.

15. The prosthetic valve of claim 1, wherein the plurality of discrete shaping members includes first and second sets of discrete shaping members; and
    wherein each discrete shaping member of the first set of discrete shaping members is inverted with respect to a discrete shaping member of the second set of discrete shaping members relative to an axis extending transverse to the longitudinal axis of the flexible covering.

16. A prosthetic valve for implantation in a body vessel having an expanded configuration and a compressed configuration, the prosthetic valve comprising:

a flexible covering defining a body region surrounding an interior lumen extending between a proximal covering end and a distal covering end, the flexible covering having an axial length extending between the proximal covering end and the distal covering end, a luminal surface defining the interior lumen, an abluminal surface, a longitudinal axis extending between the proximal covering end and the distal covering end, and a circumference extending around the abluminal surface;

a plurality of discrete shaping members individually attached to only the flexible covering, each of the discrete shaping members comprising a discontinuous Z-stent segment having a V-shape with a first free end, a second free end, and an apex, each of the Z-stent segments extending only partially around the circumference of the flexible covering, the plurality of discrete shaping members being adapted to move circumferentially relative to one another along the abluminal surface of the flexible covering when the prosthetic valve is moved between the compressed configuration and the expanded configuration; and at least one valve member operatively connected to the luminal surface, the at least one valve member adapted to modify fluid flow through the interior lumen;

where the interior lumen has a larger cross-sectional area in at least a portion surrounding the at least one valve member than at the proximal covering end and the distal covering end to create an artificial sinus; and where each of the first free end, second free end, and apex of each Z-stent segment is disposed on the flexible covering between the proximal covering end and the distal covering end.

17. The prosthetic valve of claim 16, further comprising a first stent attached near the proximal covering end and a second stent attached near the distal covering end.

18. The prosthetic valve of claim 16, wherein each discrete shaping member consists of a discontinuous Z-stent segment consisting of a V-shape.

19. The prosthetic valve of claim 16, wherein each discontinuous Z-stent segment is bowed.

20. The prosthetic valve of claim 19, wherein the plurality of discrete shaping members creates the artificial sinus.

21. The prosthetic valve of claim 16, wherein the plurality of discrete shaping members includes first and second sets of discrete shaping members; and wherein each discrete shaping member of the first set of discrete shaping members is inverted with respect to a discrete shaping member of the second set of discrete shaping members relative to an axis extending transverse to the longitudinal axis of the flexible covering.

* * * * *